United States Patent [19]

Tsukaya

[11] 4,273,111
[45] Jun. 16, 1981

[54] ENDOSCOPE WITH BEND ANGLE CONTROL

[75] Inventor: Takashi Tsukaya, Hachioji, Japan

[73] Assignee: Olympus Optical Co., Ltd., Tokyo, Japan

[21] Appl. No.: 101,076

[22] Filed: Dec. 7, 1979

[30] Foreign Application Priority Data

Dec. 22, 1978 [JP] Japan .................. 53/158869

[51] Int. Cl.³ .................. A61B 1/06; A61M 25/00
[52] U.S. Cl. .................. 128/6; 128/660;
128/772; 128/DIG. 9; 254/134.3 FT; 356/241
[58] Field of Search .................. 128/3-8,
128/DIG. 9, 772, 663, 660; 350/96.26;
254/134.3 FT; 250/358 P, 227; 15/104.3 SN;
33/302; 73/623, 634; 356/241

[56] References Cited

U.S. PATENT DOCUMENTS

| 3,744,906 | 7/1973 | Sato et al. | 128/6 |
| 3,817,089 | 6/1974 | Eggleton et al. | 73/623 |
| 4,054,128 | 10/1977 | Seufert et al. | 128/DIG. 9 |
| 4,176,662 | 12/1979 | Frazer | 128/6 |
| 4,199,258 | 4/1980 | Dau | 356/241 |

FOREIGN PATENT DOCUMENTS

| 2504663 | 8/1976 | Fed. Rep. of Germany | 128/4 |
| 50-25083 | 3/1975 | Japan | 128/4 |
| 53-42481 | 4/1978 | Japan | 128/4 |

*Primary Examiner*—Robert W. Michell
*Assistant Examiner*—Arthur S. Rose

[57] ABSTRACT

An endoscope which comprises a distal end portion (14) containing an observation optical system, a flexible tube (10), and a freely bendable section (12). In the endoscope a plurality of supersonic transducers (20) are spatially arranged on the peripheral wall of the distal end portion, and a bend angle control device (100) is further provided which controls the angle through which the freely bendable section is to be bent in accordance with output data from the plural supersonic transducers in order to direct the distal end portion to the substantial center of the cross section of, for example, the large intestine. The distal end portion is automatically directed to the substantial center of the large intestine in order to prevent the distal end portion from forcefully pressing the inner wall of the large intestine.

4 Claims, 13 Drawing Figures

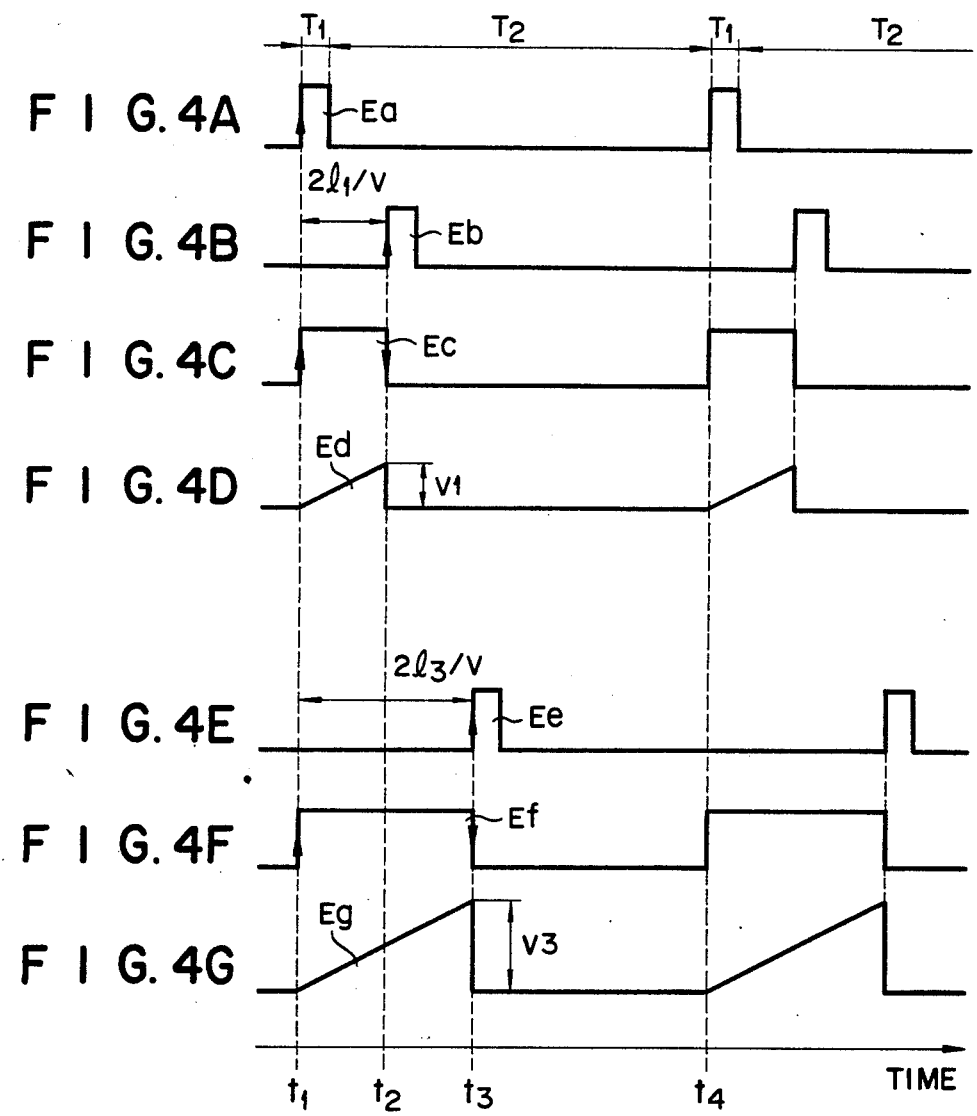

ENDOSCOPE WITH BEND ANGLE CONTROL

BACKGROUND OF THE INVENTION

This invention relates to an endoscope inserted into an intricately twisted coeliac tube.

Difficulties are often encountered in manually inserting an endoscope into the digestive tract of a living body to effect, for example, medical examination. The difficulties chiefly arise from the intricately twisted form of the digestive tract, for example, the large intestine. Therefore, it has hitherto been necessary to try to frequently control the direction in which the distal end portion of an endoscope, for example, a colon scope is inserted into the colon in conformity to the intricately twisted form of the colon in order to effect the smooth full insertion of said instrument. However, the above-mentioned control sometimes caused the distal end portion of the endoscope to forcefully press the inner wall of the colon, thus imparting great pain to a patient, and unavoidably prolonging the time of examination.

SUMMARY OF THE INVENTION

This invention has been accomplished in view of the above-mentioned circumstances, and is intended to provide an endoscope whose distal end portion, when inserted into a coeliac tube, can always be so controlled as to be directed to the center of the cross section of the coeliac tube.

To this end, the present invention provides an endoscope which comprises:

a distal end portion containing an observation optical system;

a flexible tube;

a freely bendable section for connecting the distal end portion to the flexible tube;

a plurality of supersonic transducers spatially arranged on the peripheral wall of the distal end portion; and a bend angle control device for controlling the angle through which the freely bendable section is to be bent in accordance with data supplied from the supersonic transducers in order to direct the distal end portion of said freely bendable section to the substantial center of the cross section of, for example, a coeliac tube to be examined.

With the endoscope of this invention arranged as described above, the distal end portion is automatically directed to the center of the cross section of a coeliac tube to be examined by the bend angle control device, thereby preventing the inner wall of the coeliac tube from being forcefully pressed by the inserted distal end portion of the endoscope. Therefore, even where the distal end portion is inserted into, for example, the colon of a patient, he is little likely to suffer unpleasant feeling or pain.

BRIEF DESCRIPTION OF THE DRAWING

FIGS. 4A to 4G jointly constitute a timing chart illustrating the operation of the bend angle control device of FIG. 3;

DETAILED DESCRIPTION OF THE PREFERRED EMBODIMENTS

Figure 1:
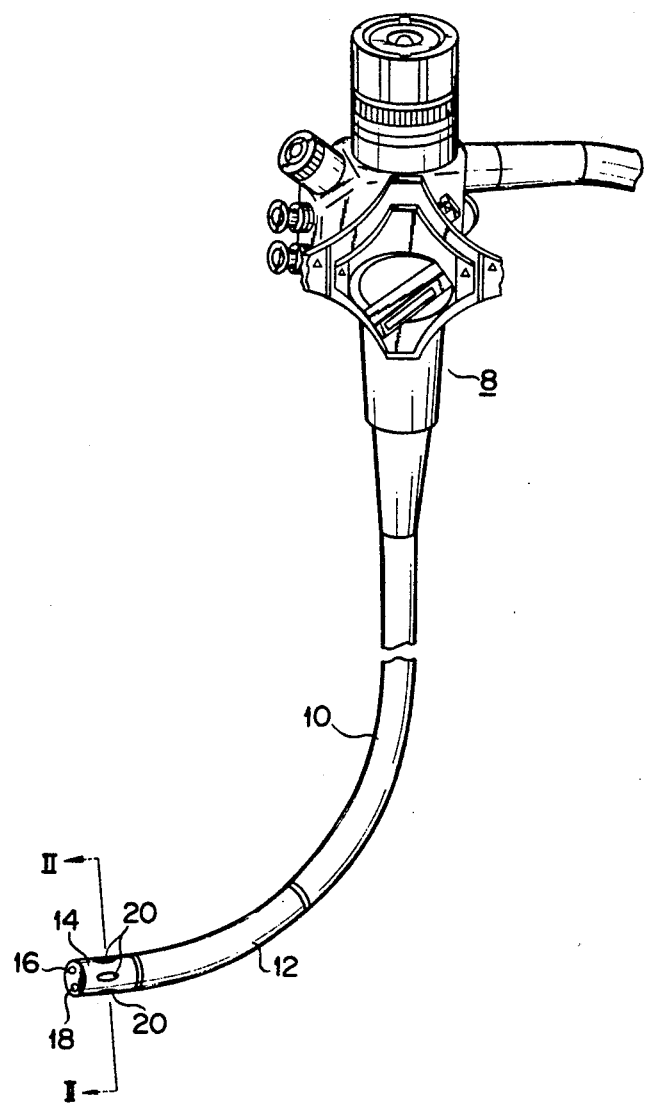
FIG. 1 is an oblique external view of an endoscope embodying this invention.

There will now be described an endoscope embodying this invention by reference to the accompanying drawing. For briefness, the same or similar parts are denoted by the same or similar reference numerals, description thereof being abridged.

Referring to FIG. 1 showing the external appearance of an endoscope embodying this invention, a flexible tube 10 connected to an operation section 8 is coupled to the distal end portion 14 through a freely bendable section 12. The tip of the distal end portion 14 is fitted with a light guide 16 and observation optical system 18. All the above-mentioned members of the endoscope of the present invention may be arranged in the same manner as those of the prior art endoscope. The peripheral wall of the distal end portion 14 has four supersonic transducers 20 arranged at an equiangular distance of 90° in the circumferential direction. The distal end portion 14 is inserted into a coeliac tube, for example, the large intestine.

Figure 2:
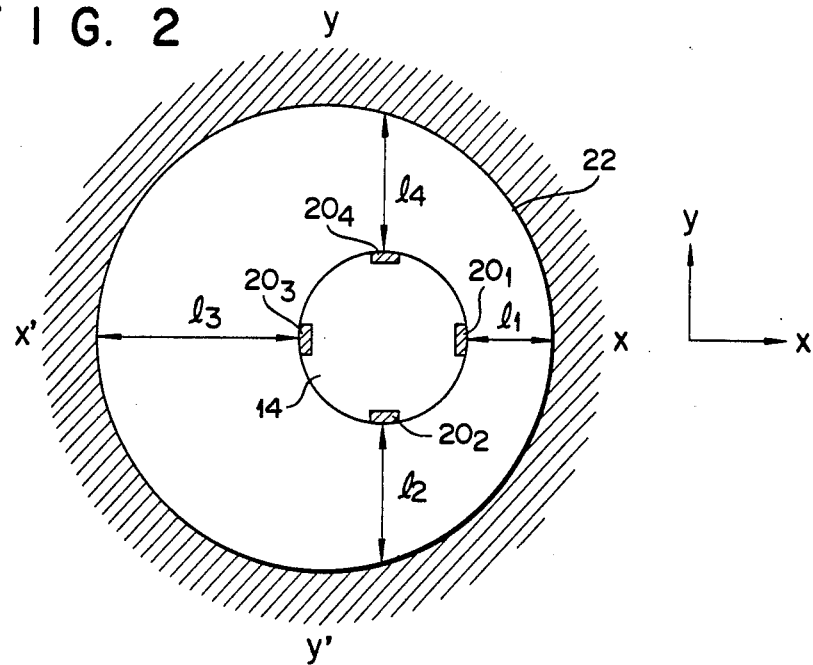
FIG. 2 is a cross sectional view on line II—II of FIG. 1 of the distal end portion 14 of the endoscope when inserted into a coeliac tube.

FIG. 2 is a cross sectional view on line II—II of the distal end portion 14 when inserted into the coeliac tube 22. Now let it be assumed that l1, l2, l3, l4 denote the distance of the supersonic transducers $20_1, 20_2, 20_3, 20_4$ from the corresponding points on the inner wall of the distal end portion 14 as measured by imaginary lines perpendicularly extended from said supersonic transducers, and that supersonic waves are issued from the respective supersonic transducers $20_1, 20_2, 20_3, 20_4$ at a speed v. Then periods extending between the points of time at which supersonic waves are produced and the points of time at which the reflections thereof are received can be respectively designated as $2l1/v, 2l2/v, 2l3/v, 2l4/v$. For briefness, the operation of the endoscope of this invention is described only by reference to the axis x, that is, a straight line connecting the supersonic transducers $20_1$ to the supersonic transducer $20_3$. However, it is to be understood that the description is applicable not only to the axes x, y but also any optional direction on an x-y plane of FIG. 2.

Figure 3:
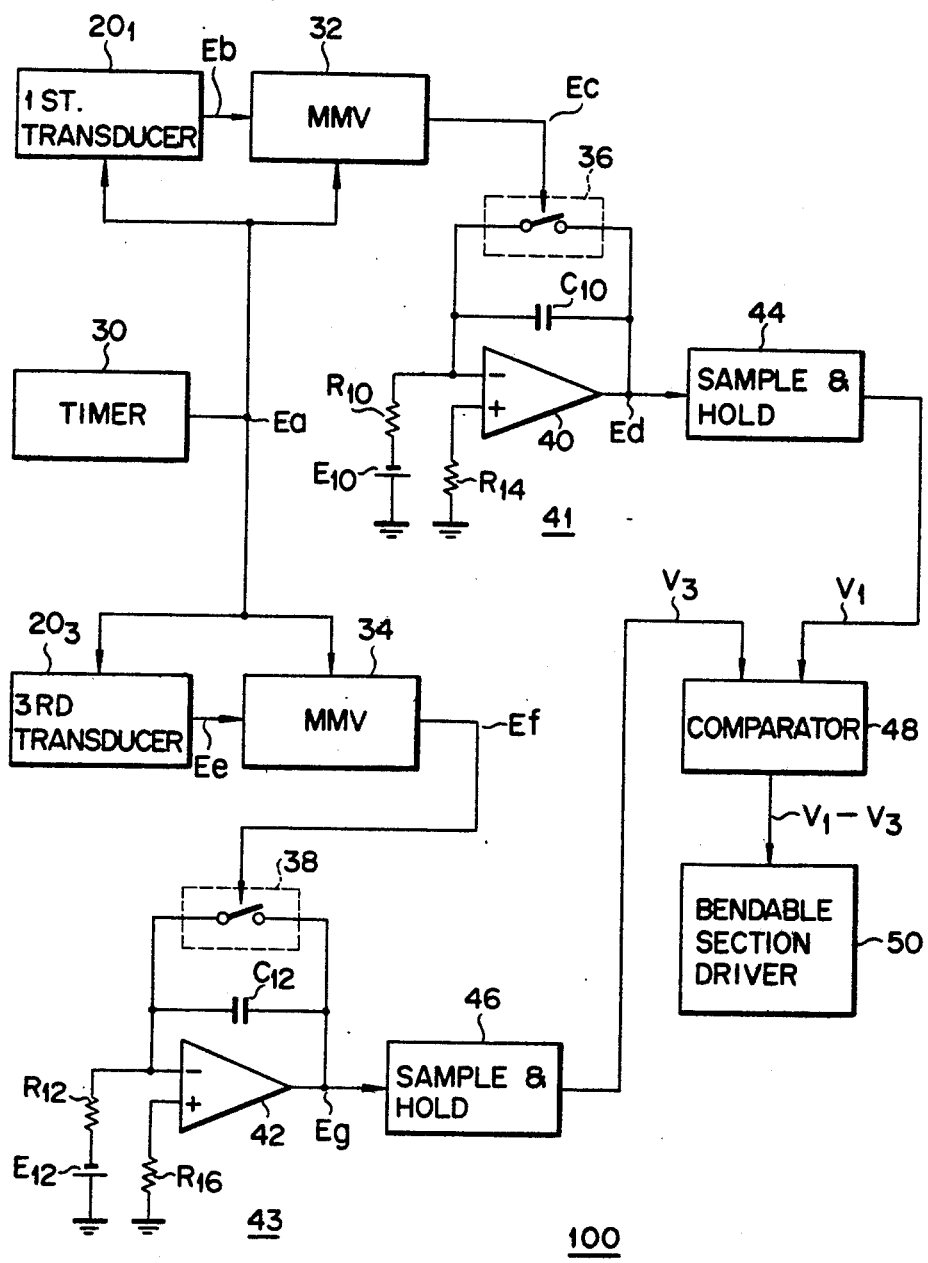
FIG. 3 is a block circuit diagram of a bend angle control device 100 for automatically controlling the angle through which the freely bendable section of the endoscope of FIG. 1 is to be bent.

FIG. 3 is a block circuit diagram of the bend angle control device 100 for controlling the position of the distal end portion 14 along the axis x of FIG. 2. There will now be described by reference to the timing chart jointly represented by FIGS. 4A to 4G the arrangement and operation of the bend angle control device 100. A timer 30 sends forth pulses Ea having a duty ratio T1:T2. The timer 30 is formed of a pulse generator which generates pulses Ea each having a pulse width T1 at a time interval T2. The pulses Ea are supplied to the first and third supersonic transducers $20_1, 20_3$, one-shot multivibrator or monostable multivibrator (abbreviated as "MMV") 32 and another MMV 34. When receiving the pulse Ea at point of time t1, the supersonic transducers $20_1, 20_3$ issue a supersonic pulse to the coeliac tube 22. At this time, the MMVs 32, 34 are triggered by the rise of the pulse Ea. When triggered, the MMVs 32, 34 respectively produce gate pulses Ec, Ef. These gate pulses Ec, Ef are respectively conducted to electronic switches 36, 38. These switches 36, 38 are each formed of, e.g., a field effect transistor (abbreviated as "FET") switch circuit.

The electronic switch 36 is connected in parallel to an integration capacitor C10. This capacitor C10 is connected between the output terminal and inverted input terminal of an amplifier 40. The inverted input terminal is connected to the negative pole of an integration input power source E10 through an integration resistor R10. The positive pole of the integration input power source E10 is grounded. The noninverted input terminal of the amplifier 40 is grounded through an offset-balance resistor R14. The amplifier 40, capacitor C10, resistors R10, R14 and power source E10 jointly constitute a Miller type integrator 41. Similarly, an amplifier 42, capacitor C12, resistors R12, R16 and power source E12 collectively form an integrator 43. The electronic switch 38 is connected in parallel to the integration capacitor C12.

When supplied with the pulse Ec, the electronic switch 36 is opened. At this time, the integrator 41 commences integration. After the point of time t1, the voltage of an integrated output signal Ed sent forth from the integrator 41 progressively rises in the form of a linear function in which time is taken as a variable. When supplied with the pulse Ef, the electronic switch 38 is opened. At this time, the integrator 43 commences the same form of integration as is carried out by the integrator 41. An integrated output signal Ed from the integrator 41, and an integrated output signal Eg from the integrator 43 are respectively delivered to sample-hold circuits 44, 46. These sample-hold circuits 44, 46 hold the peak voltages of the output integrated signals Ed, Eg which increase with time.

Where, at point of time t2, a supersonic wave reflected from the coeliac tube 22 is returned to the first supersonic transducer $20_1$, then this transducer $20_1$ generates a reset pulse Eb, which resets the MMV 32. As a result, the gate pulse Ec is extinguished. At the extinction of this gate pulse Ec, the electronic switch 36 is closed again, causing an integrated output signal Ed from the integrator 41 to be reset to the zero level. In other words, the integration time of the integrator 41 is indicated as t2−t1. This time interval t2−t1 corresponds to the aforesaid 2l1/v. The voltage V1 of the integrated output signal Ed occurring immediately before the point of time t2 at which the integration is brought to an end is held in the sample-hold circuit 44. The voltage V1 is proportional to the time interval t2−t1, and consequently 2l1/v. In other words, the distance l1 can be represented by the voltage V1.

Similarly, where, at a point of time t3, a supersonic wave reflected from the coeliac tube 22 is returned to the third supersonic transducer $20_3$, then this transducer $20_3$ generates a reset pulse Ee. When this reset pulse Ee is supplied to the MMV 34, then the integration operation of the integrator 43 is brought to an end. The integration time of the integrator 43 is t3−t1. This time interval t3−t1 corresponds to the aforesaid 2l3/v. The voltage V3 of the integrated output signal Eg produced immediately before the point of time t3 is held in the sample-hold circuit 46. Since the voltage V3 is proportional to the aforesaid 2l3/v, the distance l3 can be denoted by the voltage V3.

The voltages V1, V3 are supplied to a comparator 48. This comparator 48 delivers a signal |V1−V3| proportional to a difference between the analog levels of the voltages V1, V3 to a bendable section driver 50. This bendable section driver 50 controls the angle through which the freely bendable section 12 is to be bent or inclined relative to the axis x so as to reduce the value of |V1−V3| to the minimum of zero. In other words, the position of the freely bendable section 12 relative to the axis x is controlled by adjusting the angle through which the freely bendable section 12 is to be bent. In other words, where the value of |V1−V3| is reduced to the minimum, then a difference between the distances expressed as |l1−l3| is also minimized. As a result, the distal end portion 14 of an endoscope is set in the substantial center of the cross section of the coeliac tube 22. The above-mentioned control of the position of the endoscope, or more particularly, the freely bendable section 12 is carried out during a period extending between a point of time at which the last sample-hold operation is brought to an end a point of time at which the pulse Ea is issued again, that is, during a time interval extending from a point of time t3 to a point of time t4. The above-mentioned bend control can be effected when a servo motor set in the operation section 8 of the endoscope (shown in FIG. 1) in a state interlockingly operable with the actuation of an operation knob is driven by the aforesaid bendable section driver 50.

Figure 5:
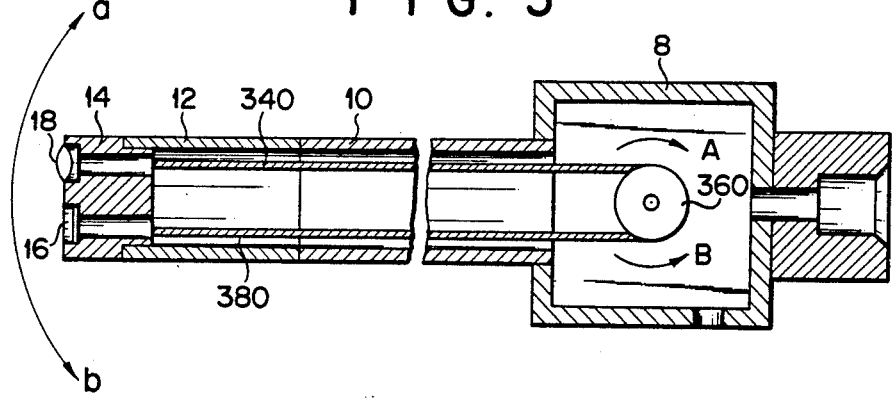
FIG. 5 is a longitudinal sectional view of a device for changing the angle through which the endoscope of FIG. 1 is to be bent when inserted into a coeliac tube.
Figure 6:
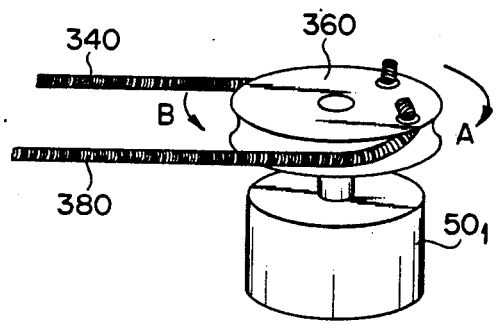
FIG. 6 is an oblique view of a servo motor section acting as the drive source of the bend angle control device of FIG. 5.

FIG. 5 is a longitudinal sectional view of a device for changing the bend angle of the freely bendable section 12. The inner end of the lateral wall on one side of the distal end portion 14 is connected to the peripheral wall on one side of a wire pulley 360 through an endoscope-bending wire 340. The inner end of the lateral wall on the opposite side of the distal end portion 14 is connected to the peripheral wall on the opposite side of the wire pulley 360 through an endoscope-bending wire 380. The wire pulley 360 is fitted, as shown in FIG. 6, to the shaft of the servo motor $50_1$. Where the servo motor $50_1$ is rotated in the direction of an arrow A indicated in FIG. 6, then the distal end portion 14 is bent in the direction of an arrow a indicated in FIG. 5. Conversely, where the servo motor $50_1$ is rotated in the direction of an arrow B indicated in FIG. 6, then the distal end portion 14 is bent in the direction of an arrow b shown in FIG. 5. In other words, the distal end portion 14 is rotated in accordance with the direction in which the servo motor $50_1$ is rotated and also the angle through which said rotation is made. The servo motor $50_1$ may be formed of not only an electric type, but also an oil pressure type. Further, a force for changing the bend angle of the distal end portion 14 may be transmitted by a fluid (oil pressure) instead of the endoscope-bending wires 340, 380. FIG. 5 shows the longitudinal sectional view of the bend angle control device set in parallel with the drawing surface. Actually, however, another bend angle control device having the same arrangement as that of FIG. 5 is provided to extend in a direction perpendicular to the drawing surface. A combination of these two bend angle control devices enables the freely bendable section 12 to be bend in any desired direction. The arrangement of the bend angle control device may be devised in various modifications. For instance, it is possible to utilize a bend angle control device set forth in the U.S. Pat. No. 4,054,128.

Description has been made of the bend angle control carried out only along the axis x. However, the same description is also applicable to the bend angle control effected along the axis y. The bend angle can be changed in any desired direction on the x-y plane by simultaneously controlling the bend angles along both axes x, y. With the embodiment of FIG. 2, four supersonic transducers $20_1$, $20_2$, $20_3$, $20_4$ are used. The concept on which this invention is based can be realized by providing a plurality of devices for detecting the distances between the various points on the peripheral surface of the distal end portion 14 of the endoscope and the inner wall of the coeliac tube 22. Even where only two supersonic transducers 20 are provided for detection of the above-mentioned distances, then it is possible to provide an endoscope which can be operated with for greater ease than the prior art manually operated endoscope. However, the above-mentioned distance-detecting devices should preferably be provided in a number of 3 or over. Where the simplicity of the construction of an endoscope is taken into account, it is best to provide three or four supersonic transducers 20.

Figure 7:
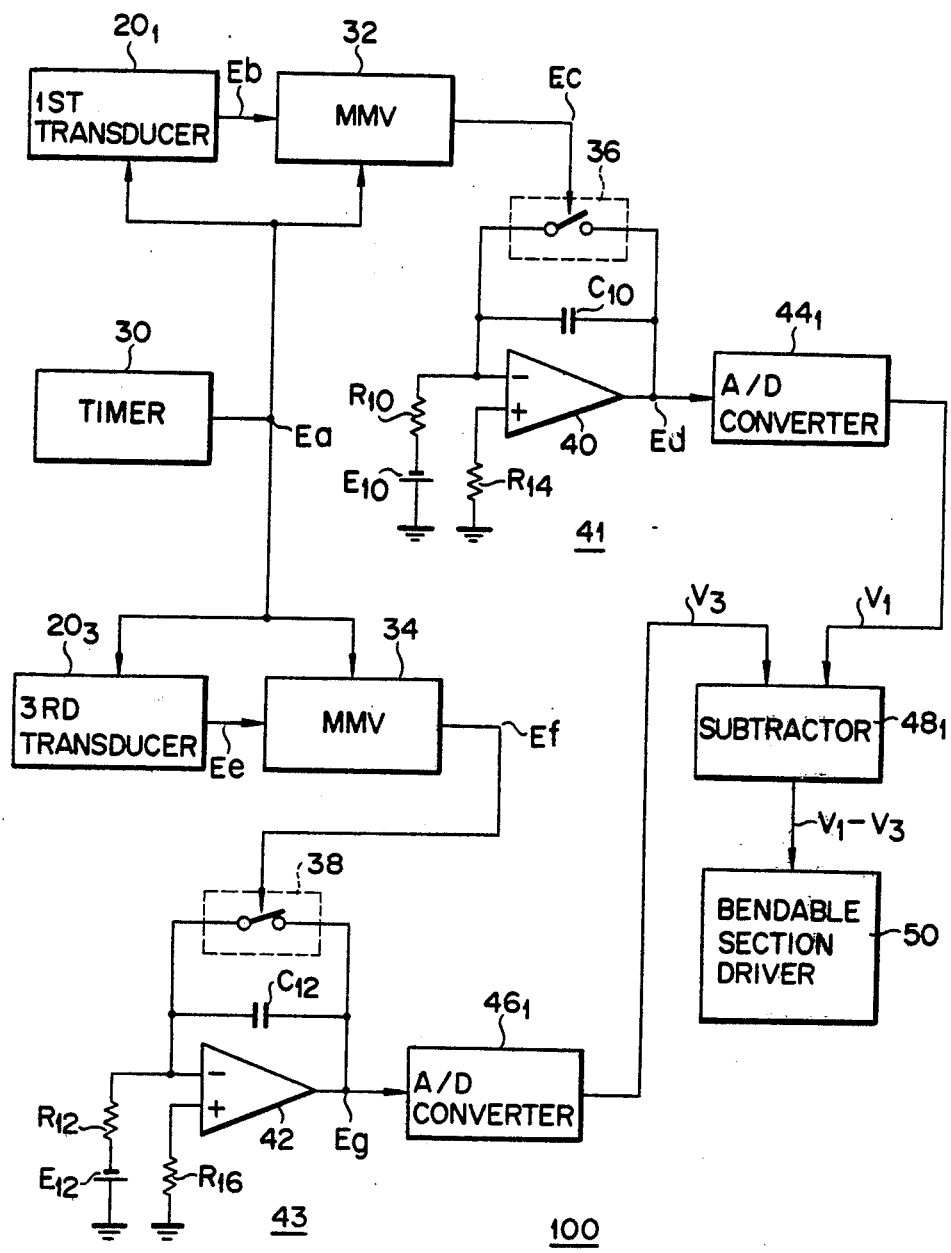
FIG. 7 is a block circuit diagram of a modification of the bend angle control device 100 of FIG. 3.

FIG. 7 is a block circuit diagram of a modification of the bend angle control device of FIG. 3. With this modification, integrated output signals Ed, Eg are converted into digital values V1, V3 by the corresponding A-D converters $44_1$, $46_1$. The digital values V1, V3 are converted by a subtractor $48_1$ into a signal denoting a difference (V1−V3) between the values represented by the above-mentioned integrated output signals. Said difference V1−V3 is converted from the digital to the analog in the bendable section driver 50. A signal denoting the result of said D-A conversion is supplied to the servo motor $50_1$ as shown in FIG. 6. In this case, the servo motor $50_1$ may be formed of a pulse motor.

With the endoscope of this invention, the insertion of the distal end portion 14 into a coeliac tube is automatically controlled to be prevented from forcefully pressing the inner wall of said coeliac tube. In other words, the direction in which the tip of the distal end portion 14 is inserted into the coeliac tube is automatically varied with the twisted form of the coeliac tube. Where observation is to be made of the interior condition of an intricately twisted coeliac tube such as the large intestine, then the endoscope of this invention can be smoothly inserted into said coeliac tube simply by being pushed. Therefore, an operator unskilled in the application of an endoscope can easily insert the endoscope of this invention. Further, the inserted tip of the distal end portion 14 does not forcefully press the inner wall of the coeliac tube, thus prominently reducing the pain which the examinee might otherwise suffer. Since the insertion of the endoscope of the invention is carried out smoothly, even the deep region of the coeliac cavity can be touched by the endoscope in a short time.

Although specific constructions have been illustrated and described herein, it is not intended that the invention be limited to the elements and constructions disclosed. One skilled in the art will recognize that the particular elements or subconstructions may be used without departing from the scope and spirit of the invention.

What is claimed is:

1. An endoscope comprising:
   (a) a distal end portion containing an observation optical system;
   (b) a flexible tube;
   (c) a freely bendable section for connecting the distal end portion to the flexible tube;
   (d) a plurality of supersonic transducers spatially arranged on the peripheral wall of the distal end portion; and
   (e) bend angle control means for controlling the angle through which the freely bendable section is to be bent in accordance with data supplied from the plural supersonic transducers in order to direct the distal end portion of said freely bendable section to the substantial center of the cross section of a coeliac tube to be examined.

2. The endoscope according to claim 1, wherein the bend angle control means comprises:
   a plurality of detection devices for producing output signals proportional to distances between the plural supersonic transducers and the corresponding points on the inner wall of a coeliac tube to be examined; and
   a device for generating a difference signal denoting a difference between the values represented by output signals from the plural detection devices, and whereby the angle through which the freely bendable section is to be bent is so controlled as to reduce said difference to the minimum.

3. The endoscope according to claim 2, wherein the difference signal-generating device comprises a comparator which compares the analog values of output signals from the detection device and issues said difference signal in accordance with the result of said comparison.

4. The endoscope according to claim 2, wherein the difference signal-generating device comprises a subtractor which arithmetically processes differences between the digital values of output signals from the detection devices, and sends forth said difference signal in accordance with the result of said arithmetic operation.

* * * * *